US009126876B2

(12) United States Patent
de Jong et al.

(10) Patent No.: US 9,126,876 B2
(45) Date of Patent: *Sep. 8, 2015

(54) FISCHER-TROPSCH PROCESS FOR CONVERTING SYNTHESIS GAS TO A LOWER OLEFIN

(75) Inventors: Krijn Pieter de Jong, Houten (NL); Adrianus Koeken, Terneuzen (NL); Matthijs Ruitenbeek, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/009,224

(22) PCT Filed: Feb. 10, 2012

(86) PCT No.: PCT/US2012/024577
§ 371 (c)(1),
(2), (4) Date: Oct. 1, 2013

(87) PCT Pub. No.: WO2012/138415
PCT Pub. Date: Oct. 11, 2012

(65) Prior Publication Data
US 2014/0024727 A1    Jan. 23, 2014

Related U.S. Application Data

(60) Provisional application No. 61/471,330, filed on Apr. 4, 2011.

(51) Int. Cl.
| | |
|---|---|
| *C07C 1/04* | (2006.01) |
| *B01J 21/04* | (2006.01) |
| *B01J 23/745* | (2006.01) |
| *B01J 35/00* | (2006.01) |
| *C10G 2/00* | (2006.01) |
| *B01J 35/10* | (2006.01) |

(52) U.S. Cl.
CPC .............. *C07C 1/046* (2013.01); *B01J 21/04* (2013.01); *B01J 23/745* (2013.01); *B01J 35/006* (2013.01); *C07C 1/044* (2013.01); *C10G 2/332* (2013.01); *B01J 35/1009* (2013.01); *B01J 35/1014* (2013.01); *C07C 2521/04* (2013.01); *C07C 2523/745* (2013.01); *C10G 2300/4006* (2013.01); *C10G 2300/4012* (2013.01); *C10G 2300/708* (2013.01); *C10G 2400/20* (2013.01)

(58) Field of Classification Search
CPC ........ C07C 1/044; C07C 11/04; C07C 11/06; C07C 1/046; C07C 2521/04; C07C 2523/745; B01J 21/04; B01J 23/745; B01J 35/006; B01J 35/1009; B01J 35/1014; C10G 2300/4012; C10G 2300/708; C10G 2400/20; C10G 2/332
USPC ......................................... 518/719
See application file for complete search history.

(56) References Cited

U.S. PATENT DOCUMENTS

| | | | |
|---|---|---|---|
| 4,478,954 A | 10/1984 | Connolly et al. | |
| 4,564,642 A | 1/1986 | Bussemeier et al. | |
| 8,703,830 B2 * | 4/2014 | Galvis et al. ................... | 518/719 |
| 2004/0077737 A1 * | 4/2004 | Eri et al. ........................ | 518/717 |
| 2012/0259026 A1 | 10/2012 | Torres Galvis et al. | |

FOREIGN PATENT DOCUMENTS

| | | |
|---|---|---|
| EP | 2314557 A1 | 4/2011 |
| GB | 1439007 A | 6/1976 |

OTHER PUBLICATIONS

Barrault, Reaction Kinetics and Catalysis Letters, 1980, vol. 15, No. 2, p. 153-158.
Bussemeier, Hydrocarbon Process, 1976, p. 105-112, Nov. 1976.
Dry, Catalysts Science and Technology, 1981, vol. 1, p. 159-197.
Dry, Catalysts Science and Technology, 1981, vol. 1, p. 198-255.
Koeken, Nano-structured catalysts for Fischer-Tropsch lower olefins synthesis; UU Progress Report Q1-Q2/2010, PL-2010-2558, Jul. 7, 2010.
Steynberg, Applied Catalysis A-General, 1999, 186, p. 41-54.
Steynberg, Studies in Surface Science and Catalysis 152, 2004, Chapter 2, p. 64-195.
PCT/US2012/024577, International Search Report and Written Opinion, Dated Jul. 5, 2012, p. 1-12.
PCT/US2012/024577, International Preliminary Report on Patentability, Dated Jul. 24, 2013, p. 1-7.
PCT/US2012/024577, Response Written Opinion, Dated Jan. 29, 2013.

* cited by examiner

*Primary Examiner* — Jafar Parsa
*Assistant Examiner* — Amy C Bonaparte

(57) ABSTRACT

Effect Fischer-Tropsch synthesis of lower olefins by converting a syngas feedstream at a temperature within a range of from 300° C. to no more than 400° C. using a supported, iron-based catalyst under a total system pressure of at least 2 megapascals with a volumetric ratio of hydrogen to carbon monoxide of at least 3:1 with markedly lower coking rates than attainable at a total system pressure of less than 2 megapascals.

8 Claims, No Drawings

FISCHER-TROPSCH PROCESS FOR CONVERTING SYNTHESIS GAS TO A LOWER OLEFIN

This application is a non-provisional application claiming priority from the U.S. Provisional Patent Application No. 61/471,330, filed on Apr. 4, 2011, entitled "FISCHER-TROPSCH PROCESS FOR CONVERTING SYNTHESIS GAS TO A LOWER OLEFIN" the teachings of which are incorporated by reference herein, as if reproduced in full hereinbelow.

This invention relates generally to production of lower olefins (i.e. those that contain from two to eight carbon atoms ($C_2$ to $C_8$)) from a feedstream comprising carbon monoxide (CO) and hydrogen ($H_2$) by means of, for example, a Fischer-Tropsch process using a supported iron-based catalyst. This invention relates particularly to such a process that comprises a specific set of process parameters that leads to substantially lower levels of carbon deposition (also known as "coking") than one encounters with the same catalyst, but with Fischer-Tropsch process parameters that differ from the specific set of process parameters.

Synthesis gas or "syngas" conventionally applies to a mixture comprising CO and $H_2$ and may include an amount of carbon dioxide ($CO_2$). Production of olefins from syngas via Fischer-Tropsch synthesis preferably includes a precursor step that involves reducing or even completely removing the $CO_2$.

Syngas production occurs via a variety of methods including steam reforming of natural gas, gasification of coal or biomass, and burning or gasification of waste materials. Environmental considerations favor use of renewable raw materials such as biomass or waste materials over non-renewable raw materials such as coal.

Fischer-Tropsch synthesis (FTS), a catalyzed chemical reaction in which one converts syngas into a range of hydrocarbons of various forms commonly employs a catalyst based on iron or cobalt, although nickel and ruthenium have also been used. FTS involves a variety of competing chemical reactions rather than a single reaction.

Lower olefins, especially those that contain two to eight carbon atoms ($C_2$ to $C_8$), preferably two to six carbon atoms ($C_2$ to $C_6$) and more preferably two to four carbon atoms ($C_2$ to $C_4$), find extensive use in the chemical industry as raw materials for a variety of processes including, but not limited to, synthesis of olefin homopolymers such as polyethylene and polypropylene as well as a variety of copolymers (e.g. linear low density polyethylene, a copolymer of ethylene and a comonomer that contains, e.g. four, six or eight carbon atoms, respectively an ethylene/butylene copolymer, an ethylene/hexene copolymer and otherwise known as an ethylene-octene copolymer, and propylene-ethylene random or block copolymers) and interpolymers (a generic term that sometimes includes copolymers (two polymerizable monomers), terpolymers (three polymerizable monomers) and tetrapolymers (four polymerizable monomers) or any larger number of copolymerizable monomers.

Iron-based catalysts find favor over cobalt-based catalysts for FTS because the former provide, relative to the latter, one or more of a) a higher yield of the lower olefins, b) a higher level of water-gas shift (WGS) activity, and c) lower cost.

Artisans skilled in heterogeneous catalysis recognize that such catalysts comprise a catalytically active part, preferably iron-based for this invention, and a catalytically non-active part or support, with the latter constituting a major (more than 50%) portion of the catalyst. This distinguishes heterogeneous catalysts from bulk catalysts wherein the support typically constitutes a minor (less than 50%) portion of the catalyst.

Co-pending patent application P87211PC00 discloses a process for producing lower olefins by converting a feed stream comprising CO and $H_2$ at a temperature above 270 degrees Celsius (° C.), preferably no higher than 500° C., using a heterogeneous or supported iron-based catalyst. The catalyst comprises iron-containing particles dispersed onto a support that is chemically inert to iron at a loading of at least 1 percent by weight (wt %), based upon weight of the support. Illustrative supports include silica, alumina, silica-alumina, titania, zirconia, magnesia, manganese oxide, metal carbides, metal nitrides, metal silicides, carbonaceous materials, synthetic clay materials, and natural clay materials with a preference for alpha-alumina, carbon nanofibers, silicon carbide or silicon nitride. The $H_2$ and CO are present in a molar ratio of $H_2$ to CO of from 0.1:1 to 10:1, preferably less than 3:1, more preferably less than 2:1 and most preferably within a range of from 0.5:1 to 1:1. Process conditions include a reaction temperature above 270° C., preferably above 290° C., more preferably above 300° C., and most preferably above 310° C., but preferably no higher than 500° C., more preferably no higher than 450° C. and most preferably no higher than 400° C. Process conditions also include a pressure of from 1 Bar (100 kilopascals (KPa) to 700 Bar (70 megapascals (MPa), preferably 5 Bar (500 KPa) to 100 Bar (10 MPa), and more preferably 10 Bar (1 MPa) to 50 Bar (5 MPa). A preferred temperature and pressure combination is 340° C. to 360° C. and 15 Bar (1.5 MPa) to 25 Bar (2.5 MPa).

FTS can be carried out in any suitable reactor selected from those known to skilled artisans, with a fluidized bed reactor or multitubular fixed bed reactor being preferred. In addition, any known catalyst loading technique suitable for the reactor may be used. Further information can be found in *Fischer-Tropsch Technology*, A. Steynberg and M. Dry (Editors), Studies in Surface Science and Catalysis 152, Chapter 2: Fischer-Tropsch Reactors, Elsevier B. V., Amsterdam (2004).

*Catalysts Science and Technology*, J. R. Anderson and M. Boudart (Editors), Chapter 4 (M. E. Dry), pages 159-256 (1981) discusses principal factors influencing loss of catalytic activity and the rate of carbon deposition on iron catalysts. At pages 195-196, the author discusses four mechanisms for loss of Fischer-Tropsch catalyst activity, one of which is loss of active area due to deposition of carbonaceous material (also known as "fouling"). At page 202, the author notes that "[w]hen carbon is deposited on iron catalysts the particles swell and also disintegrate. At page 206, the author refers to a finding that there is a relationship between carbon deposition rate and a ratio of partial pressure of CO to partial pressure of $H_2$ at the reactor entrance. Following Table 16, the author observes that as total pressure increases and the $H_2$:CO ratio increases, carbon deposition rates drop.

British Patent (GB) 1 439 007 teaches, in part, that at a given partial pressure for CO, it is possible to decrease the rate of carbon deposition by only increasing the partial pressure of hydrogen. The patentee works with pressures of from 32 kilograms per square centimeter (3.14 MPa) to 70 (6.86 MPa) and temperatures of from 280° C. to 450° C., preferably from 305° C. to 330° C. The patentee shows, in Table 1, that as total pressure and the $H_2$:CO ratio increase, the carbon deposition rate decreases. The patentee works with a "pure" iron catalyst modified with potassium, the catalyst sometimes being referred to as a "bulk" catalyst in contrast to a supported catalyst that is used in this invention. In an example, the patentee reports a carbon deposition of 2.6 grams of carbon per 100 grams of iron per 100 hours, which equates to $6\times10^{-9}$ moles of carbon per gram of iron per second.

Skilled artisans understand that heterogeneous catalysts comprise two parts, a catalytically active part and a catalytically inactive part, also known as a support, with the latter part constituting more than 50 percent by weight (wt %), based upon total catalyst weight, of the catalyst, with weight percentages as high as 90 wt % or more being common By way of contrast, in a bulk catalyst, the catalytically inactive part constitutes less than 50 wt %, based upon total catalyst weight, with weight percentages of 10 wt % or less being common. Skilled artisans recognize that, as between bulk iron catalysts and supported iron catalysts, differences in structure and iron content contribute to a difference in coking behavior of the catalysts.

In some aspects, this invention is an improved process for producing lower olefins by conversion of a feed stream comprising carbon monoxide and hydrogen at a temperature within a range of from greater than 300° C. to no more than 400° C. using a supported, iron-based catalyst that comprises iron-containing particles dispersed onto a support that is chemically inert toward iron with a loading of at least 1 weight percent based upon total catalyst weight, wherein the improvement comprises effecting the conversion at a combination of a) a total system pressure of at least 20 Bars (2 megapascals), b) a volumetric ratio of hydrogen to carbon monoxide of at least 3:1, and c) a hydrogen partial pressure of at least 15 Bar (1.5 megapascals), whereby the catalyst has a coke formation rate after four hours time on stream of less than $1\times10^{-7}$ moles of carbon per gram of catalyst per second.

In some aspects, the improved process further comprises feedstream gas hourly space velocity within a range of from greater than 15,000 $hr^{-1}$ to less than 170,000 $hr^{-1}$.

The improved process employs a temperature within a range of from greater than 300° C. to no more than 400° C., preferably from 320° C. to 380° C.

The improved process includes a volumetric ratio of hydrogen to carbon monoxide of at least 3:1, preferably at least 4:1, and more preferably at least 5:1.

The improved process yields a coke formation rate after four hours time on stream of less than $1\times10^{-7}$ moles of carbon per gram of catalyst per second, preferably less than or equal to $8.5\times10^{-8}$ moles of carbon per gram of catalyst per second, more preferably less than or equal to $6.0\times10^{-8}$ moles of carbon per gram of catalyst per second, and still more preferably less than or equal to $3.5\times10^{-8}$ moles per gram of catalyst per second, even more preferably less than or equal to $1\times10^{-9}$ moles of carbon per gram of catalyst per second.

In succeeding paragraphs, Arabic Numerals designate examples (Ex) representative of the present invention while capital letters refer to comparative examples (CEx).

Prepare an alpha-alumina ($\alpha$-$Al_2O_3$) supported iron (Fe) catalyst via aqueous incipient wetness impregnation at ambient pressure using a solution that contains 5.5 milliliters (mL) demineralized water and 2.94 grams (g) ammonium iron(III) citrate (green powder, 14.5-16 weight percent (wt %) Fe) and 4 g of $\alpha$-$Al_2O_3$ (BASF Nederland BV, sieve fraction 0.212 millimeter (mm) to 0.425 mm, BET surface area of 8.1 square meters per gram ($m^2/g$), and pore volume of 0.5 cubic centimeters per gram ($cm^3/g$)). After each impregnation step, dry the catalyst at ambient temperature (nominally 25° C.) and a pressure of 60 millibars (mbar) (6 KPa) for two hours. Alternatively, after each impregnation stip dry the catalyst at 120° C. in static air at atmospheric pressure. After incorporating all of the solution on the support through successive impregnation-drying cycles, dry the impregnated $\alpha$-$Al_2O_3$ under flowing air at 90 C for one hour, then calcine it at 500° C. for two hours, ramping from 90° C. to 500° C. at a rate of 5° C. per minute, then switch off heating and allowing it to cool to ambient temperature.

The calcined material has an iron oxide ($Fe_2O_3$) crystallite size of 25 nanometers (based on X-ray powder diffraction (XRD) using a $CoK_\alpha$ radiation source and the $Fe_2O_3$ peak measured at a two-thetha angle of 38.9°), a surface area of 15 $m^2/g$. Based on X-ray fluorescence spectroscopy (XRF), the calcined material contains 84.8 wt % $\alpha$-$Al_2O_3$, 14.1 wt % $Fe_2O_3$ (9.9 wt % Fe), 0.48 wt % sodium (Na), 0.071 wt % sulfur (S), with the remainder of the composition made up by trace amounts of the oxides of silicium, calcium, chromium and manganese, each wt % being based upon total calcined material weight.

Reduce the calcined material for 3.2 hours at 350° C. with a mixture of 20 volume percent (vol %) $H_2$ and 80 vol % argon, each vol % being based upon total mixture volume, flowing at a space velocity of 140 liters per gram of catalyst per hour ($L \cdot g_{cat}^{-1} \cdot h^{-1}$).

Subject portions of the catalyst to FTS conditions as shown in Table 1 below where $p_{H2}$ and $p_{CO}$ represent, respectively, hydrogen partial pressure and carbon monoxide partial pressure in the feed stream. Summarize results in Table 2 below wherein "HC" means hydrocarbon, "WTY" means weight time yield as expressed in $10^{-6}$ moles of CO converted into hydrocarbons ($C_1$-$C_8$) per gram of catalyst per second ($10^{-6} \cdot mol_{CO} \cdot g_{cat}^{-1} \cdot s^{-1}$), the coke formation rate is expressed in $10^{-6}$ moles of carbon formed per gram of catalyst per second ($10^{-6} \cdot mol_C \cdot g_{cat}^{-1} \cdot s^{-1}$), $C_2$-$C_4$ means two carbon atoms to four carbon atoms, and $C_5$-$C_8$ means five carbon atoms to eight carbon atoms. All selectivity values are expressed in terms of weight percent (wt %), based upon the analysis of the $C_1$-$C_8$ hydrocarbon products and normalized to the weight of $C_1$-$C_8$ hydrocarbon products (carbon products with one carbon atom up to eight carbon atoms, excluding $CO_2$) in the product stream on a carbon dioxide free basis.

TABLE 1

| Ex/CEx | Pressure (bar/MPa) | T (° C.) | Space velocity ($h^{-1}$) | $H_2$/CO (vol. basis) | $p_{H2}$ (bar/MPa) | $p_{CO}$ (bar/MPa) |
|---|---|---|---|---|---|---|
| A | 10/1 | 350 | 86000 | 1 | 5.0/0.5 | 5.0/0.5 |
| B | 10/1 | 350 | 85000 | 2 | 6.7/0.67 | 3.3/0.33 |
| C | 10/1 | 350 | 85000 | 5 | 8.3/0.83 | 1.7/0.17 |
| D | 20/2 | 350 | 84000 | 1 | 10.0/1.0 | 10.0/1.0 |
| E | 20/2 | 350 | 85000 | 2 | 13.3/1.33 | 6.7/0.67 |
| 1 | 20/2 | 350 | 84000 | 5 | 16.7/1.67 | 3.3/0.33 |
| F | 5/0.5 | 350 | 55000 | 1 | 2.5/0.25 | 2.5/0.25 |
| G | 10/1 | 350 | 114000 | 3 | 7.5/0.75 | 2.5/0.25 |
| H | 15/1.5 | 350 | 169000 | 5 | 12.5/1.25 | 2.5/0.25 |
| I | 12.5/1.25 | 350 | 143000 | 4 | 10.0/1.0 | 2.5/0.25 |
| J | 12/1.2 | 350 | 170000 | 5 | 10.0/1.0 | 2.0/0.2 |
| K | 13.3/1.33 | 350 | 180000 | 3 | 10.0/1.0 | 3.3/0.5 |
| L | 15/1.5 | 350 | 209000 | 2 | 10.0/1.0 | 5.0/0.5 |
| M | 20/2 | 350 | 274000 | 1 | 10.0/1.0 | 10.0/1.0 |
| 2 | 20/2 | 350 | 88000 | 3 | 15/1.5 | 5.0/0.8 |
| 3 | 20/2 | 350 | 92000 | 4 | 16/1.6 | 4.0/0.4 |
| N | 20/2 | 350 | 28000 | 1 | 10.0/1.0 | 10.0/1.0 |
| 4 | 20/2 | 350 | 17000 | 5 | 16.7/1.67 | 3.3/0.33 |
| 5 | 20/2 | 350 | 168000 | 5 | 16.7/1.67 | 3.3/0.33 |
| 6 | 20/2 | 320 | 82000 | 5 | 16.7/1.67 | 3.3/0.33 |
| 7 | 20/2 | 380 | 82000 | 5 | 16.7/1.67 | 3.3/0.33 |

TABLE 2

Overview of results at the respective Fischer Tropsch conditions mentioned in Table 1.

| Ex/CEx | Time on stream, TOS (h) | CO conversion to HC (%) | Weight Time Yield WTY$^a$ ($10^{-6}$ mol$_{CO}$·g$_{cat}^{-1}$·s$^{-1}$) | Coke formation rate ($10^{-6}$ mol$_C$·g$_{cat}^{-1}$·s$^{-1}$) | Selectivity (wt %) | | | | | | | |
|---|---|---|---|---|---|---|---|---|---|---|---|---|
| | | | | | methane | ethane | ethene | propene | 1-butene | $C_2$-$C_4$ olefins | $C_2$-$C_4$ paraffins | $C_5$-$C_8$ |
| A | 4.0 | 3.2 | 16 | 1.46 | 17 | 1.9 | 16 | 20 | 12 | 50 | 3.9 | 30 |
| B | 4.1 | 6.9 | 23 | 0.944 | 17 | 1.8 | 13 | 17 | 11 | 44 | 3.9 | 36 |
| C | 4.0 | 21 | 36 | 0.398 | 30 | 5.4 | 13 | 17 | 7.7 | 40 | 8.5 | 21 |
| D | 2.0 | 21 | 107 | 5.31 | 15 | 2.5 | 12 | 18 | 11 | 43 | 5.0 | 37 |
| E | 4.0 | 29 | 98 | 0.415 | 13 | 2.0 | 12 | 18 | 12 | 44 | 4.4 | 39 |
| 1 | 4.0 | 37 | 62 | <0.001 | 16 | 2.5 | 15 | 20 | 12 | 49 | 5.5 | 30 |
| F | 4.0 | 0.82 | 2.7 | 1.12 | 24 | 2.2 | 20 | 21 | 10 | 54 | 3.9 | 19 |
| G | 4.0 | 15 | 50 | 0.802 | 22 | 3.6 | 13 | 17 | 9.0 | 43 | 6.3 | 29 |
| H | 4.0 | 31 | 103 | 0.225 | 20 | 4.1 | 13 | 19 | 10 | 45 | 7.3 | 28 |
| I | 4.0 | 25 | 84 | 0.500 | 21 | 3.3 | 13 | 18 | 11 | 44 | 6.0 | 29 |
| J | 4.1 | 23 | 77 | 0.395 | 24 | 4.1 | 13 | 17 | 9.3 | 42 | 6.9 | 27 |
| K | 4.0 | 18 | 98 | 0.731 | 16 | 2.1 | 13 | 18 | 11 | 44 | 4.5 | 35 |
| L | 4.0 | 18 | 147 | 1.45 | 15 | 2.0 | 12 | 17 | 12 | 43 | 4.4 | 38 |
| M | 1.1 | 7.8 | 129 | 5.08 | 14 | 1.9 | 12 | 17 | 11 | 42 | 4.1 | 40 |
| 2 | 4.1 | 26 | 68 | 0.059 | 14 | 1.8 | 13 | 18 | 12 | 45 | 4.3 | 37 |
| 3 | 4.0 | 29 | 64 | <0.001 | 14 | 1.9 | 14 | 19 | 12 | 47 | 4.6 | 34 |
| N | 4.1 | 34 | 57 | 1.72 | 20 | 8.2 | 7.8 | 19 | 7.6 | 40 | 13 | 27 |
| 4 | 4.1 | 51 | 17 | <0.001 | 17 | 3.0 | 15 | 20 | 12 | 49 | 6.0 | 27 |
| 5 | 4.0 | 25 | 84 | 0.033 | 16 | 2.2 | 14 | 18 | 12 | 46 | 5.0 | 33 |
| 6 | 4.1 | 21 | 35 | <0.001 | 13 | 2.0 | 13 | 18 | 12 | 45 | 5.2 | 37 |
| 7 | 4.1 | 41 | 68 | 0.081 | 21 | 3.6 | 14 | 19 | 11 | 46 | 6.5 | 27 |

The data in Table 2 show that with a total pressure of 20 bar (2 MPa) and a $H_2$/CO ratio of at least 3:1, a very low coking rate (less than $1\times10^{-7}$ mol$_C$·g$_{cat}^{-1}$·s$^{-1}$, and in several instances less than $1\times10^{-9}$ mol$_C$·g$_{cat}^{-1}$·s$^{-1}$, is evident at the temperature and space velocities shown in Table 1. By way of contrast, even at similar space velocities, a reduction in total pressure (e.g. to 10 bar/1 MPa as in CEx A-C) even at the same $H_2$/CO volumetric ratio (e.g. 5 as in CEx C) yields substantially higher coking rates ($3.98\times10^{-7}$ mol$_C$·g$_{cat}^{-1}$·s$^{-1}$ for CEx C as compared to less than $1\times10^{-9}$ mol$_C$·g$_{cat}^{-1}$·s$^{-1}$ for Ex 1 at similar space velocities and the same temperature. A comparison of Ex 1 (space velocity of 84000 $h^{-1}$) with Ex 4 (space velocity of 17000 $h^{-1}$) shows that, all other conditions being the same or nearly the same, one achieves a coking rate of less than $1\times10^{-9}$ mol$_C$·g$_{cat}^{-1}$·s$^{-1}$ at two disparate space velocities notwithstanding an art recognized trend to increase coking rate as space velocity increases. The catalyst performance data in Table 2 show that the catalysts of Ex 1 through 7 show activity in terms of WTY and selectivity to desired products, namely ethene and propene.

What is claimed is:

1. An improved Fischer-Tropsch process for producing lower olefins by conversion of a feed stream comprising carbon monoxide and hydrogen at a temperature within a range of from greater than 300° C. to no more than 400° C. using a supported, iron-based catalyst that consists essentially of iron-containing particles dispersed onto a support that is chemically inert toward iron, with a loading of such particles of at least 1 weight percent based upon total catalyst weight, wherein the improvement comprises selecting as the support an alpha alumina, and effecting the conversion at a combination of a) a total system pressure of at least 20 Bars (2 megapascals), b) a volumetric ratio of hydrogen to carbon monoxide of at least 3:1, and c) a hydrogen partial pressure of at least 15 Bar (1.5 megapascals), whereby conversion at the combination leads to substantially lower levels of coking on the catalyst than one encounters with the same catalyst, but with Fischer-Tropsch process parameters that differ from the combination, the substantially lower levels of coking on the catalyst being a coke formation rate after four hours time on stream of less than $1\times10^{-7}$ moles of carbon per gram of catalyst per second.

2. The improved process of claim 1, wherein the combination further comprises a feed stream gas hourly space velocity within a range of from greater than 15,000 hr$^{-1}$ to less than 170,000 hr$^{-1}$.

3. The improved process of claim 1, wherein the temperature range is from 320° C. to 380° C.

4. The improved process of claim 1, wherein the volumetric ratio of hydrogen to carbon monoxide is at least 4:1.

5. The improved process of claim 4, wherein the volumetric ratio of hydrogen to carbon monoxide is at least 5:1.

6. The improved process of claim 1, wherein the coke formation rate after four hours time on stream is less than or equal to $8.5\times10^{-8}$ moles of carbon per gram of catalyst per second.

7. The improved process of claim 6, wherein the coke formation rate after four hours time on stream is less than or equal to $6.0\times10^{-8}$ moles of carbon per gram of catalyst per second.

8. The improved process of claim 7, wherein the coke formation rate after four hours time on stream is less than or equal to $3.5\times10^{-8}$ moles of carbon per gram of catalyst per second.

* * * * *